US009630017B1

(12) United States Patent
Buchheit (10) Patent No.: US 9,630,017 B1
(45) Date of Patent: Apr. 25, 2017

(54) SAFETY FEATURE TO DISABLE AN AUTOMATED EXTERNAL DEFIBRILLATOR (AED) WHEN USED ON A PERSON HAVING A WIRELESS IMPLANTABLE MEDICAL DEVICE (IMD)

(71) Applicant: Brian K. Buchheit, Davie, FL (US)

(72) Inventor: Brian K. Buchheit, Davie, FL (US)

(*) Notice: Subject to any disclaimer, the term of this patent is extended or adjusted under 35 U.S.C. 154(b) by 0 days.

(21) Appl. No.: 14/613,829

(22) Filed: Feb. 4, 2015

Related U.S. Application Data

(60) Provisional application No. 62/090,141, filed on Dec. 10, 2014, provisional application No. 62/091,673, filed on Dec. 15, 2014, provisional application No. 62/091,682, filed on Dec. 15, 2014, provisional application No. 62/093,148, filed on Dec. 17, 2014, provisional application No. 62/093,551, filed on Dec. 18, 2014.

(51) Int. Cl.
*A61N 1/00* (2006.01)
*A61N 1/39* (2006.01)

(52) U.S. Cl.
CPC ......... *A61N 1/3931* (2013.01); *A61N 1/3968* (2013.01); *A61N 1/3987* (2013.01)

(58) Field of Classification Search
CPC .......................................... A61N 1/39–1/3993
See application file for complete search history.

(56) References Cited

U.S. PATENT DOCUMENTS

| 4,787,389 A * | 11/1988 | Tarjan | A61N 1/3962 607/14 |
| 2004/0127774 A1* | 7/2004 | Moore | A61N 1/3925 600/300 |
| 2008/0004663 A1* | 1/2008 | Jorgenson | A61N 1/37247 607/5 |
| 2010/0023095 A1* | 1/2010 | Stevenson | A61N 1/08 607/63 |

* cited by examiner

*Primary Examiner* — Scott Getzow
(74) *Attorney, Agent, or Firm* — Patents on Demand P.A.; Brian K. Buchheit; Scott M. Garrett (57) ABSTRACT

A system for minimizing adverse effects to an implanted medical device (IMD) can include an automated external defibrillator and an IMD safety control. The automated external defibrillator can have a shock function having the potential to adversely affect a treatment provided by and/or the operation of the implanted medical device. The implanted medical device can be embedded within a living body, referred to as an implantee. The implanted medical device can include wireless communication capabilities. The IMD safety control can be coupled to the automated external defibrillator and can be configured to disable performance of the shock function upon the implantee when the shock function is activated and enable performance of the shock function upon resolution by an operator of the automated external defibrillator. The IMD safety control can be capable of wireless communication with the implanted medical device.

17 Claims, 5 Drawing Sheets

SAFETY FEATURE TO DISABLE AN AUTOMATED EXTERNAL DEFIBRILLATOR (AED) WHEN USED ON A PERSON HAVING A WIRELESS IMPLANTABLE MEDICAL DEVICE (IMD)

CROSS-REFERENCE TO RELATED APPLICATIONS

This application claims priority to, and fully incorporates herein, the following provisional applications: application No. 62/090,141, filed Dec. 10, 2014 entitled "Enabling Wireless Transmission Between and External Computing Device and an Implanted Medical Device Via Body Tissue Conduction"; application No. 62/091,673, filed Dec. 15, 2014 entitled "Utilizing a Subdermal Wireless Antenna to Provide Signal Gain for Wireless Communication Between an Implanted Medical Device and an External Device"; application No. 62/091,682, filed Dec. 15, 2014 entitled "Securing Implanted Medical Device Communications"; application No. 62/093,148, filed Dec. 17, 2014 entitled "Enabling Safe Mode For Implanted Medical Devices"; application No. 62/093,551, filed Dec. 18, 2014 entitled "Temporarily Replacing IMD Component Functionality with External Device Equivalent Functionality".

BACKGROUND

The present invention relates to the field of medical devices and, more particularly, to a safety feature to disable an automated external defibrillator (AED) when used on a person having an implanted medical device (IMD).

External defibrillators have been commonly used in hospital settings to treat cardiac arrhythmias for decades. As cities and populations have expanded and congested, it has become more difficult for a person experiencing a sudden cardiac arrest (SCA) to reach a hospital or receive medical attention from emergency responders in a timely manner. Many deaths attributed to SCA are preventable when defibrillation is administered within 3-5 minutes of onset.

This has led to the development and positioning of automated or semi-automated external defibrillators (AEDs) in key public and private locations where access to a person experiencing a SCA is limited like a large sports venue. The concept is simple; the AED guides a layperson in life-saving tasks (e.g., CPR, electrode-pad placement, etc.) until emergency support arrives.

The proliferation of AEDs, however, is headed on a collision course with another advancement of medical technology—implanted medical devices. Implantable medical devices (IMDs) are a subset of medical devices that are partially or totally inserted into a human body for a prolonged period of time (i.e., over thirty days). Pacemakers, neurostimulators, cochlear implants, and insulin pumps are some common examples of IMDs that extend the life and/or enhance the quality of life of millions of people.

It is not always obvious when a person has an IMD. Using an AED on a person with an IMD is known to cause damage or changes in operation to the IMD as well as the person. Currently, the layperson is relied upon to notice physical indicators (e.g., scars, lumps, identification bracelets, etc.), which can be well hidden or easily overlooked in such a stressful and time-sensitive situation.

BRIEF SUMMARY

One aspect of the present invention can include a system for minimizing adverse effects to an implanted medical device caused by an automated external defibrillator. Such a system can include an automated external defibrillator and an IMD safety control. The automated external defibrillator can have a shock function that has the potential to cause an adverse effect to a treatment provided by an implanted medical device (IMD) and/or the operation of the implanted medical device. The implanted medical device can be embedded within a living body, herein referred to as an implantee. The adverse effect can occur when the shock function is performed upon the implantee. The implanted medical device can include wireless communication capabilities. The IMD safety control can be coupled to the automated external defibrillator and can be configured to disable performance of the shock function upon the implantee when the shock function is activated and enable performance of the shock function upon resolution by an operator of the automated external defibrillator. The IMD safety control can be capable of wireless communication with the implanted medical device.

Another aspect of the present invention can include a method for mitigating interference of an automated external defibrillator with operation of an implanted medical device (IMD). Such a method can begin with the detection of an implanted medical device within a living body, herein referred to as an implantee, by an IMD safety control module coupled with the automated external defibrillator, in response to the attachment of the automated external defibrillator to the implantee. Performance of a shock function by the automated external defibrillator can be known to have a potential to cause adverse effects to a treatment provided by the implanted medical device and/or operation of the implanted medical device. The implanted medical device can be an active implanted medical device having wireless communication capabilities. A communication pathway can be established with the detected implanted medical device. The communication pathway for wireless communication can refer to any communication medium not requiring a dedicated physical wire between communication endpoints over which an information bearing signal is conveyed. The performance of the shock function of the automated external defibrillator can be disabled. The disabling can occur automatically, by default, responsive to a wireless communication between the automated external defibrillator and the implanted medical device via the established communication pathway and does not require visual inspection of the implantee by an operator of the automated external defibrillator for post-operation indicators for the implanted medical device and/or an indicia for the implanted medical device worn by the implantee. A resolution can be requested from the operator of the automated external defibrillator to accommodate the implanted medical device detected within the implantee. Upon receipt of the resolution, performance of the shock function by the automated external defibrillator can be enabled.

Yet another aspect of the present invention can include a computer program product that includes a computer readable storage medium having embedded computer usable program code. The computer usable program code can be configured to, in response to an attachment of an automated external defibrillator to a living body having an implanted medical device embedded therein, herein referred to as an implantee, detect the implanted medical device (IMD) of the implantee. Performance of a shock function of the automated external defibrillator can be known to have a potential to cause adverse effects to a treatment provided by the implanted medical device and/or operation of the implanted medical device. The implanted medical device can be an active implanted medical device having wireless communication capabilities. The computer usable program code can be configured to establish a communication pathway with the detected implanted medical device. The communication pathway for wireless communication can refer to any communication medium not requiring a dedicated physical wire between communication endpoints over which an information bearing signal is conveyed. The computer usable program code can be further configured to disable performance of the shock function of the automated external defibrillator. The disabling can occur automatically, by default, responsive to a wireless communication between the automated external defibrillator and the implanted medical device via the established communication pathway. The computer usable program code can be configured to request resolution from the operator of the automated external defibrillator to accommodate the implanted medical device detected within the implantee. The computer usable program code configured to, upon receipt of said resolution, enable performance of the shock function by the automated external defibrillator.

DETAILED DESCRIPTION

This disclosure provides for a solution for mitigating the adverse effects of the shock function administered by an automated external defibrillator upon an implanted medical device (IMD) located within the person being treated. An IMD safety control can be coupled with the electronic device in order to disable performance of the shock function when the implanted medical device is detected within the person being treated. An operator of the electronic device can be notified of the presence of the implanted medical device and resolution requested. The shock function can be enabled upon receipt of the resolution. In one embodiment, bidirectional communications can occur between the IMD safety control and/or automated external defibrillator and the implanted medical device, which enable either/both devices to change their state and/or trigger functions to ensure maximum safety. For example, an implanted medical device can immediately go into a "safe" mode right before the automated external defibrillator emits the electric shock, and the implanted medical device can immediately go back "online" (out of the "safe" mode) after the shock to ensure proper regulation of the person's body (such as their heart rhythm) post-charge. This lack of automatic safeguard results in severe physical ramifications to people having implanted medical devices when oversights occur.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
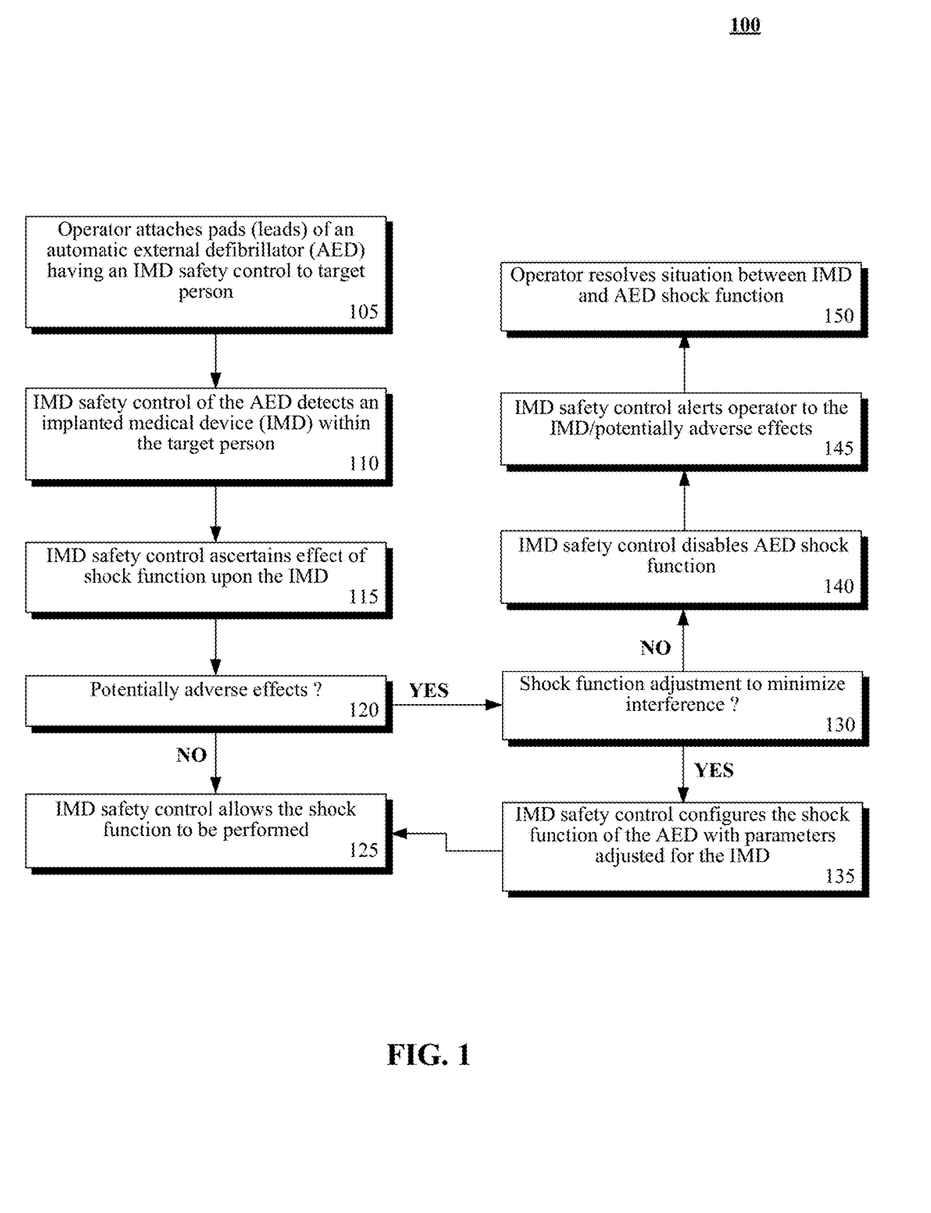
FIG. 1 is a flowchart of a method describing the general use of an automated external defibrillator having an implantable medical device (IMD) safety control in accordance with an embodiment of the disclosure.

Referring to the figures, FIG. 1 is a flowchart of a method 100 describing the general use of an automated external defibrillator having an implantable medical device (IMD) safety control in accordance with an embodiment of the disclosure. The general purpose of the IMD safety control can be to minimize the occurrence of potentially adverse interactions caused by the shock function of the automated external defibrillator and the operation of the IMD.

As used herein, the term "automated external defibrillator" can refer to a portable electronic device that is capable of automatically diagnosing ventricular fibrillation and ventricular tachycardia and treating these cardiac arrhythmias using defibrillation (i.e., an electric shock function) externally applied to a patient's or target person's body. Such an automated external defibrillator can be fully automated (i.e., does not require an operator to initiate the shock function) or can require manual initiation (i.e., pressing a button), with or without prompting by the automated external defibrillator.

It is well known in the Art that electrical interference (e.g., electro-magnetic, radio-frequency, electro-shocks, etc.) has the potential to adversely affect operation of an implanted medical device. An increase in electrical interference, as a whole, can be anticipated within many commonly-utilized environments due to the proliferation of wireless electronic devices and related electronic systems. At the same time, advances in medical science can increase the use of implanted medical devices to treat a variety of ailments. Therefore, it can be easily deduced that the likelihood of environmental electrical interference with the operation of implanted medical devices will also increase.

The increased availability of automated external defibrillators in public settings can represent a specific example of electrical interference poised to become commonplace. The use of an automated external defibrillator can directly apply the electric shock and the electrical interference it causes in very close proximity to the implanted medical device. That is, the electric shock provided by the automated external defibrillator can pass much closer to or through the implanted medical device than other sources of electrical interference.

Method 100 can begin in step 105 where an operator attaches the pads or leads of an automated external defibrillator having an IMD safety control to a target person. Step 105 can assume that the automated external defibrillator was already retrieved from a storage location and brought within an operational distance to the target person. The target person can be a living human who has embedded within their body an implanted medical device like a pacemaker or implantable cardioverter defibrillator (ICD). Within these Figures, the term "target person" can be used interchangeably with the term "implantee".

Further, it can also be assumed that the automated external defibrillator can detect the attachment of the pads to the target person, automatically through one or more inherent functions or via input from the operator, and that this detection can be conveyed to or otherwise obtained by the IMD safety control.

The IMD safety control of the automated external defibrillator can detect the implanted medical device within the target person in step 110. It can be important to note that the operator of the automated external defibrillator is not required to perform any task to detect the implanted medical device, as is currently required by conventional approaches and prior art like U.S. Pat. No. 8,548,584B2. Step 110 can utilize the functionality of the automated external defibrillator.

In an emergency situation where seconds count, even a trained operator of the automated external defibrillator can overlook physical indicators that the target person has an implanted medical device. Further, advances in surgical techniques and implanted medical device technology can minimize these physical indicators, making it more difficult for the operator of the automated external defibrillator to notice.

In step 115, the IMD safety control can ascertain the effect of the shock function upon the detected implanted medical device. For example, St. Jude Medical recognizes that the shock delivered via external cardioversion/defibrillation can cause, in pacemakers and ICDs, loss of capture, transient inhibition, asynchronous noise reversion pacing, damage to the electrode-tissue interface, operational change to a backup VVI mode, and damage to the IMD circuitry. Such adverse effects can cause problems for the target person of varying severity.

The IMD safety control can determine if the shock function will have any potentially adverse effects, either directly to the implanted medical device (e.g., electrical interference) or indirectly via physiological changes to the target person (e.g., medication delivered) in step 120. Step 120 can encompass use of a rating scale to represent a magnitude of the potential adverse effect with respect to the specific implanted medical device and/or emergency medical condition.

When it is determined that the function will have no potentially adverse effects, the IMD safety control can allow the automated external defibrillator to perform the shock function in step 125.

When the shock function has the potential to adversely affect the implanted medical device or target person, step 130 can be performed where the IMD safety control can determine if parameters of the shock function can be adjusted to minimize the amount of electrical interference with the implanted medical device while still providing the life-saving shock function. Step 130 can require that the automated external defibrillator is capable of having one or more parameters (e.g., shock voltage, shock time, etc.) of the shock function adjusted.

When the shock function can be adjusted to minimize electrical interference, the IMD safety control can configure the shock function of the automated external defibrillator with parameters adjusted for the implanted medical device in step 135. From step 135, method 100 can flow to step 125 where the IMD safety control can allow the shock function to be performed on the target person.

When the shock function cannot be adjusted to minimize electrical interference, step 140 can be performed where the IMD safety control can disable the shock function of the automated external defibrillator. The IMD safety control can then alert the operator to the implanted medical device and/or the potentially adverse effects in step 145.

In step 150, the operator can resolve the situation between the implanted medical device and shock functional of the automated external defibrillator. For example, the operator can adjust the placement of the pads on the target person's body to direct the flow of electricity away from the implanted medical device.

It should be emphasized that an automated external defibrillator without the IMD safety control would perform the shock function, regardless; potentially harming the target person and/or the implanted medical device.

Figure 2:
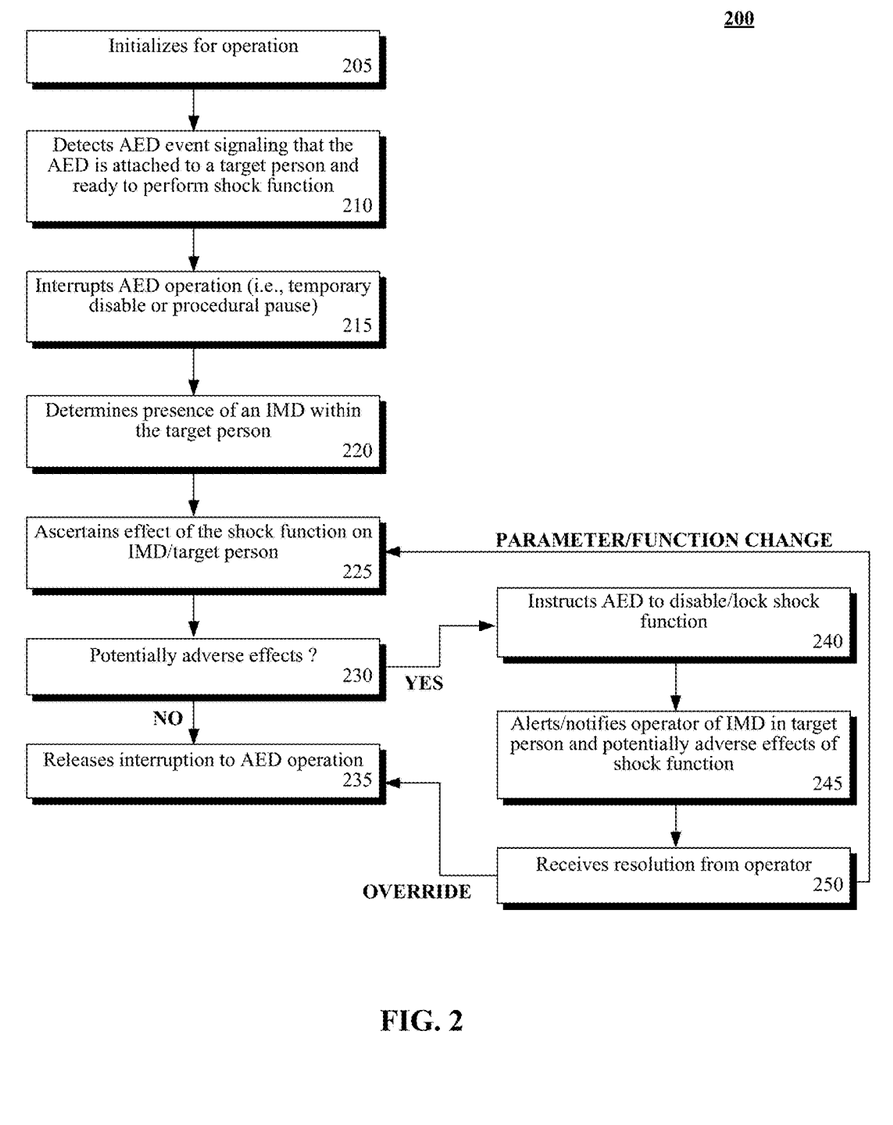
FIG. 2 is a flowchart of a method describing the general operation of the IMD safety control in conjunction with an automated external defibrillator (AED) in accordance with an embodiment of the disclosure.

FIG. 2 is a flowchart of a method 200 describing the general operation of the IMD safety control in conjunction with an automated external defibrillator (AED) in accordance with an embodiment of the disclosure. Method 200 can represent one or more steps taken by the IMD safety control in method 100

Method 200 can begin in step 205, where the IMD safety control can initialize for operation. In step 210, an event indicating that the automated external defibrillator is attached to a target person and is ready to perform a shock function can be detected. Such events can include, but are not limited to, function calls, button presses, menu selections, data signals, and the like.

Operation of the automated external defibrillator can be interrupted by the IMD safety control in step 215. For example, the automated external defibrillator can be placed in a stand-by state or mode, the shock function can be temporarily disabled, or an algorithm or procedure of the automated external defibrillator can be paused (i.e., data or trigger for next step can be withheld).

In step 220, the presence of an implanted medical device within the target person can be determined. The detection of the implanted medical device described in step 220 can be performed in a variety of ways, such as methods 255 and 270 of FIG. 2A. Method 255 can represent simple implanted medical device detection, whereas method 270 can be a more complex means of detection using waveform analysis.

Figure 2A:
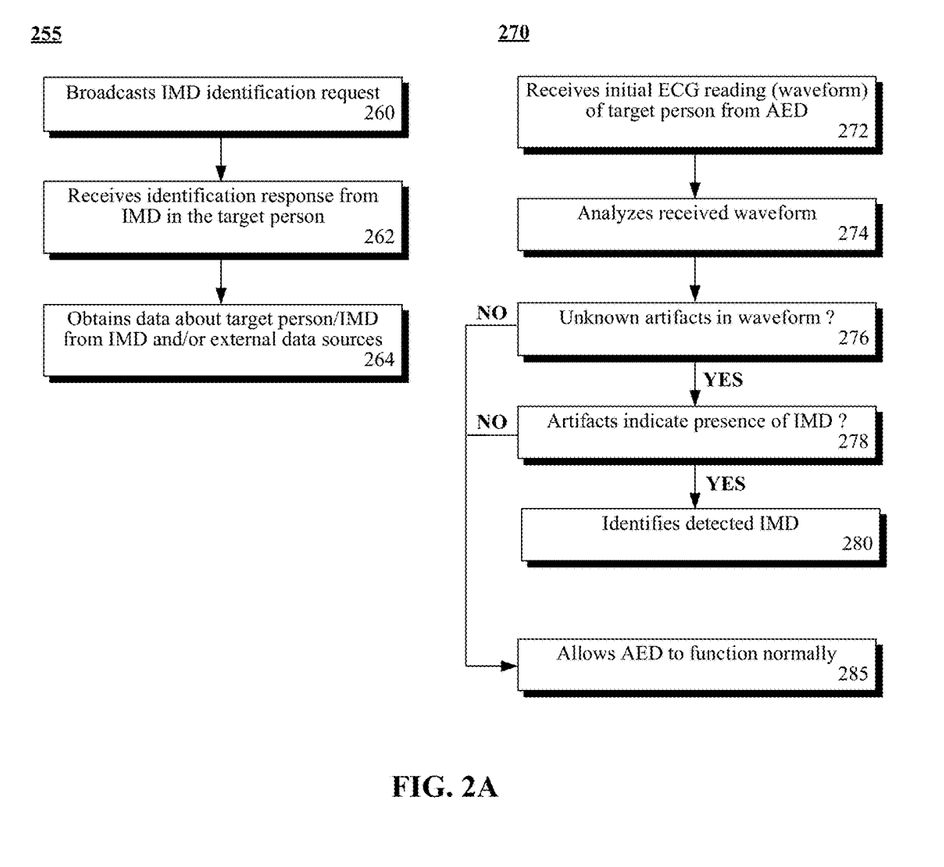
FIG. 2A is a collection of flowcharts detailing exemplary methods for the IMD safety control to detect an implanted medical device in accordance with an embodiment of the disclosure.

Method 255 can begin in step 260 where the IMD safety control can broadcast an identification request to any and all implanted medical devices within a predefined range upon known, applicable communication channels. Step 260 can assume that the automated external defibrillator or IMD safety control and the implanted medical device have wireless communication capability.

An identification response can be received from an implanted medical device embedded within the target person in step 262. Step 262 can include the receipt of multiple identification responses, one for each implanted medical device within the target person. In step 264, data about the target person and/or the implanted medical device can be obtained from the implanted medical device and/or external data sources.

The information obtained in step 264 can be extremely helpful in treating the target person. For example, if the implanted medical device is a pacemaker or ICD, the pacemaker or ICD can indicate what pacing/defibrillation has already been administered without rectifying the arrhythmia. This information can assist the IMD safety control and/or automated external defibrillator in determining the parameters needed to treat the target person.

Alternately, method 270 can begin in step 272 where the IMD safety control can receive the initial electrocardiogram (ECG) reading, which is a waveform, of the target person from the automated external defibrillator. It can be assumed that the automated external defibrillator began collecting ECG data for the target person once the pads were attached in order to begin its own analysis for treatment. Should the automated external defibrillator not automatically collect ECG data for the target person, step 272 can be expanded to request collection of this information from the automated external defibrillator.

The received waveform can be analyzed in step 274. Such analysis can include filtering expected abnormal cardiac activity to focus on unknown or extraneous artifacts of the waveform. In step 276, it can be determined if the analysis identified unknown artifacts in the waveform.

When it is determined that there are unknown artifacts present in the waveform, the unknown artifacts can be further assessed to determine if the artifacts indicate the presence of an implanted medical device in step 278. Artifacts can be introduced in ways other than an implanted medical device, such the performance of CPR, agonal breathing, and handling or movement of the target person.

When it is determined that the unknown artifacts indicate that an implanted medical device is within the target person, step 280 can be performed where the detected implanted medical device can be identified by its artifact signature. The identification of step 280 can be achieved in a variety of ways like comparing the unknown artifacts in the waveform to a library of known waveforms or to sets of known waveform parameters of various implanted medical devices.

When the waveform does not contain unknown artifacts or the unknown artifacts do not indicate the presence of an implanted medical device, method 270 can proceed to step 285 where the automated external defibrillator can be allowed to function normally. Execution of step 285 can also terminate the performance of method 200.

The analyses performed in method 270 and/or can be performed local to the IMD safety control and/or automated external defibrillator, performed by a remotely-located computer system (i.e., cloud service, processing server, etc.), or a combination thereof. Further, additional data required for these analyses can also be local and/or remotely-located.

Returning to method 200, once the IMD safety control has determined the presence of an implanted medical device within the target person in step 220, the effect of the shock function on the implanted medical device and/or target person in step 225. In step 230, the possibility of the shock function having potentially adverse effects upon the implanted medical device and/or target person can be determined.

When it is determined that the shock function will not have an adverse effect upon the implanted medical device, step 235 can execute where the interruption to operation of the automated external defibrillator can be released, allowing normal function. When it is determined that the shock function will have an adverse effect upon the implanted medical device, the automated external defibrillator can be instructed to disable or lock the shock function in step 240.

In an alternate embodiment, step 240 can lock the entirety of the automated external defibrillator except for select input/output functionality.

In step 245, the operator can be alerted and/or notified of the implanted medical device in the target person and the potentially adverse effects that the shock can cause the implanted medical device and/or target person. Resolution from the operator can then be received in step 250.

When the received resolution is to override the lock-out, method 200 can flow from step 250 to step 235 where the interruption to the automated external defibrillator's operation can be released. Override resolution can require additional inputs such as supervisory identification and/or a password. When the received resolution is to change to a different function, if possible, or one or more parameters of the shock function (i.e., a different function is selected or function parameters are selected), method 200 can flow from step 250 to step 225 where the modified function can be assessed for potentially adverse effects upon the implanted medical device.

Another resolution can be for the operator to decide to not use the implanted medical device on the target person (i.e., perform the function manually), which is not explicitly shown in method 200. However, such resolution can be handled as a function change where the change is to cancel execution of the function and method 200 can then terminate after step 250.

Further, method 200 can be expanded to account for situations where minimizing interference of the electric shock with the implanted medical device is not effectively possible. As an example, the IMD safety control can detect the target person has a neurostimulator implanted on their spinal cord. Currently, manufacturers of neurostimulators cannot advise a means for safely using an external defibrillator in a person with any type of neurostimulator. Therefore, the adverse effect of the automated external defibrillator can be weighed against the value or necessity of performing the shock function.

In such an example, steps 240 and 245 can be performed, however, the operator may not be provided with the means to provide resolution, except for in the case where the operator is a trained medical professional and can provide authorization to the IMD safety control to override. Additional steps can then be included for the IMD safety control to use the automated external defibrillator to monitor the target person's cardiac condition until the point in time where withholding the shock function poses a greater adverse health impact than the adverse effects on the neurostimulator. The threshold can vary based on the specific type of neurostimulator and approved medical guidelines. At such a point in time, the IMD safety control can then ignore step 250 and execute step 235 to automatically perform the shock function.

This type of weighted decision-making can be applied to all implanted medical devices, not just neurostimulators, as used in this example.

Figure 3:
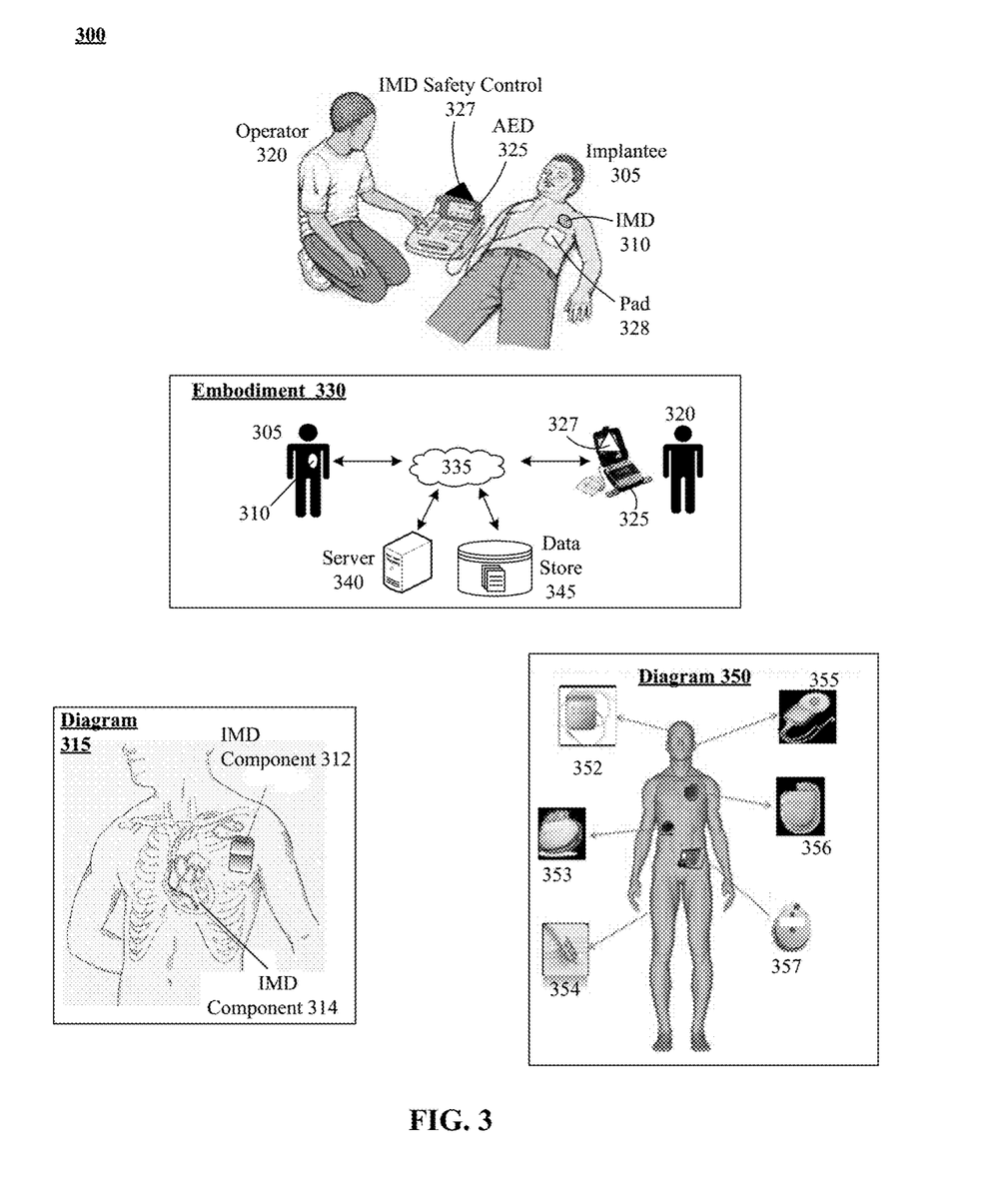
FIG. 3 is an illustration depicting an implantee having an implanted medical device being treated with an automated external defibrillator (AED) equipped with an IMD safety control in accordance with an embodiment of the disclosure.

FIG. 3 is an illustration 300 depicting an implantee 305 having an implanted medical device 310 being treated with an automated external defibrillator (AED) 325 equipped with an IMD safety control 327 in accordance with an embodiment of the disclosure. The steps of methods 100, 200, 255, and/or 270 can be performed within the context of illustration 300.

The implanted medical device 310 can include wireless communication abilities. As shown in embodiment 330, the implanted medical device 310 can wirelessly communicate via a network 335 with one or more devices connected to the network 335. These devices can include a server 340, a network data store 345, and/or an automated external defibrillator 325 controlled by an operator 320. Communications over the network 335 with the implanted medical device 310 can be unidirectional or bidirectional, depending on implementation specifics. Additionally, communications can be active, semi-active, or passive from the perspective of the implanted medical device 310, in various embodiments. The automated external defibrillator 325 can receive the information about the implantee 305 and/or the implanted medical device 310 directly, indirectly (i.e., through server 340 or data store 345), or both depending on the specific embodiment of the disclosure.

As used herein, a medical device can be a manufactured product used to cope with human disease, care for human injuries, meet human anatomical needs, maintain human anatomical needs, maintain or monitor human physiological functions, support or sustain human life, control human conception, or examine specimens or from human bodies. An implanted medical device 310 can be a medical device that is partially or totally inserted into the human body or natural orifice and is expected to stay in there for thirty days or more. Additionally, implanted medical device 310 can be a medical device used to replace an epithelial surface or the surface of the eye that is expected to stay in place for thirty days or more. Surgical or medical procedures can be used to insert or apply implanted medical devices 310 and surgical or medical procedures can be used to remove implanted medical devices 310.

The implanted medical device 310 can be an active or passive device. An active implanted medical device 310 can be an implanted medical device that uses electrical energy or other power to make it function. Devices that are powered by the human body or by gravity are not generally considered active implanted medical devices by this definition. Human body powered and/or gravity powered implanted medical devices 310 are to be considered passive implanted medical devices 310, which are included within the scope of embodiments of the disclosure.

Diagram 350 visually depicts a non-exclusive listing of implanted medical devices 310 capable of implantation within the human body of implantee 305. These implanted medical devices 310 can include neurostimulators 352 (e.g., cortical stimulators, deep brain stimulators, spinal cord stimulators and vagus nerve stimulators, sacral nerve stimulation, etc.), gastric stimulators 353, foot drop and other skeletal implants 354, cochlear implants 355, cardiac implants 356 (e.g., cardioverter-defibrillator, cardiac resynchronization device, cardiac defibrillators, pacemakers, etc.), medication pumps 357 (e.g., insulin pumps, morphine pumps, etc.), bone fusion stimulators, and the like.

The implanted medical device 310 can be a single, discrete device implanted in the implantee 305, or can consist of two or more components. For example, diagram 315 showing the body of implantee 305 illustrates that implanted medical device 310 can include two different components; IMD component 312 and IMD component 314. More specifically, an implantable cardioverter defibrillator (ICD) is shown, where component 312 is the pulse generator and component 314 is the electrode or lead that is inserted into the heart of the implantee 305.

Many existing standards exist that provide definitions and standards for implanted medical devices 310, which are to be selectively considered as applicable to the present disclosure to the extent that they define implanted medical devices 310 and to the extent these definitions are consistent with embodiments of the disclosure. To elaborate, the International Organization for Standards (ISO) has established TC 150 for implants for surgery: more specifically TC150/SC1 (subcommittee for materials), TC150/SC2 (subcommittee for cardiovascular implants and extracorporeal systems), TC 150/SC3 (subcommittee for Neurosurgical implants), TC 150/SC4 (subcommittee for bone and joint replacements), TC 150/SC5 (subcommittee for Osteosynthesis and spinal devices), TC 150/SC6 (subcommittee for active implants), and TC 150/SC7 (subcommittee for tissue-engineered medical products). Documents for these subcommittees and definitions contained therein are to be considered applicable for definitions of implanted medical devices 310, as used and defined in embodiments of the disclosure. For example, ISO 13485:2003 "Medical Devices—quality management systems—requirements for regulator purposes" is applicable to embodiments of the disclosure for implanted medical devices 310. Appreciably, these standards are not to be construed as limiting the scope of the disclosure, but are useful for providing additional definitional material and specifics not expressly detailed herein, but which are to be considered as having been contemplated by the disclosure.

The automated external defibrillator 325 can include, at least, components for delivering an electric shock to the implantee 305. As shown in illustration 300, the automated external defibrillator 325 can be of a portable nature. The automated external defibrillator 325 is typically connected to the implantee 305 by means of two pads 328 having electrodes that act as the terminal points of the electric shock. Thus, the placement of the pads 328 on the body of the implantee 305 can be crucial for minimizing interference with and/or damage to the implanted medical device 310.

The IMD safety control 327 can represent the hardware and/or software components required to detect the implanted medical device 310 within the implantee 305 and prohibit administering the electric shock by the automated external defibrillator 325 should the shock pose additional danger to the implantee 305 and/or implanted medical device 310, as discussed in method 100.

For example, in one embodiment, the IMD safety control 327 can be a logic circuit built into the automated external defibrillator 325; in another embodiment, the IMD safety control 327 can be a software program that interacts with the software that controls operation of the automated external defibrillator 325.

In its simplest form, the IMD safety control 327 can be thought of as an automated "kill switch" for the automated external defibrillator 325, suspending defibrillation of the automated external defibrillator 325 when an implanted medical device 310 is detected within the implantee 305 and/or too close to the pads 328.

For example, the anterior-apex scheme, as shown in illustration 300, can be the pad 328 placement typically suggested by the manual and/or prompts of the automated external defibrillator 325. The anterior-apex scheme can position both pads 328 on the front of the chest at opposite ends of a diagonal line; one pad 328 by the right clavicle and the other pad 328 by the bottom, left side of the ribcage. The electric shock can flow through the space of the implantee's 305 body between the pads 328, which includes the heart.

Thus, an operator 320 would place the pads 328 in this default position on the implantee's 305 chest. However, this placement can cause significant damage to any implanted medical device 310 within or proximate to the path of the electric shock, such as an insulin pump implanted on the left-side of the abdomen. In this situation, upon detecting the insulin pump 310, the IMD safety control 327 can guide the operator 320 in placing the pads 328 using the anterior-posterior scheme; one pad 328 on the front of the chest to the upper-left of the sternum and the other pad 328 on the back behind the heart, under the right scapula. Using this position scheme, the shock provided by the automated external defibrillator 325 can travel front-to back and not as close to the insulin pump 310, minimizing interference.

As another example, the IMD safety control 327 can instruct the operator 320 to visually inspect the general location of the implantee's 305 body where a detected implanted medical device 310 would be implanted and to ensure that the pads 328 are positioned the recommended at least one inch away from the implanted medical device 310.

Embodiment 330 can illustrate a robust implementation of the IMD safety control 327. In embodiment 330, the IMD safety control 327 can wirelessly communicate with the implanted medical device 310, server 340 and/or data store 345 over the network 335 to collect additional information about the implantee 305 and/or implanted medical device 310, as well as data regarding the interaction of the automated external defibrillator 325 with implanted medical device 310.

For example, upon detection of the implanted medical device 310, the IMD safety control 327 can establish a communication link to the implanted medical device 310 over the network 335 to acquire basic patient and/or operational data. From the acquired data, the IMD safety control 327 can then obtain safety or interaction information about the specific implanted medical device 310 from a trusted data source 345 like the Web site of the implanted medical device 310 manufacturer or an applicable governing body. Such information can then be used by the IMD safety control 327 to determine if the implantee 305 and/or implanted medical device 310 are at risk for an adverse interaction with the shock function of the automated external defibrillator 325.

The network 335 can represent one or more discrete wireless communication pathways. For example, the automated external defibrillator 325 can utilize a wireless telemetry signal to communicate with the implanted medical device 310 and wireless network connection to communicate with server 340 and/or data store 345. Network 335 connectivity and/or communications can be subject to typical standards and/or practices like authentication, encryption, and the like, which the implanted medical device 310, automated external defibrillator 325, and/or IMD safety control 327 are compatible.

As used herein, presented data store 345 can be a physical or virtual storage space configured to store digital information. Data store 345 can be physically implemented within any type of hardware including, but not limited to, a magnetic disk, an optical disk, a semiconductor memory, a digitally encoded plastic memory, a holographic memory, or any other recording medium. Data store 345 can be a stand-alone storage unit as well as a storage unit formed from a plurality of physical devices. Additionally, information can be stored within data store 345 in a variety of manners. For example, information can be stored within a database structure or can be stored within one or more files of a file storage system, where each file may or may not be indexed for information searching purposes. Further, data store 345 can utilize one or more encryption mechanisms to protect stored information from unauthorized access.

Figure 4:
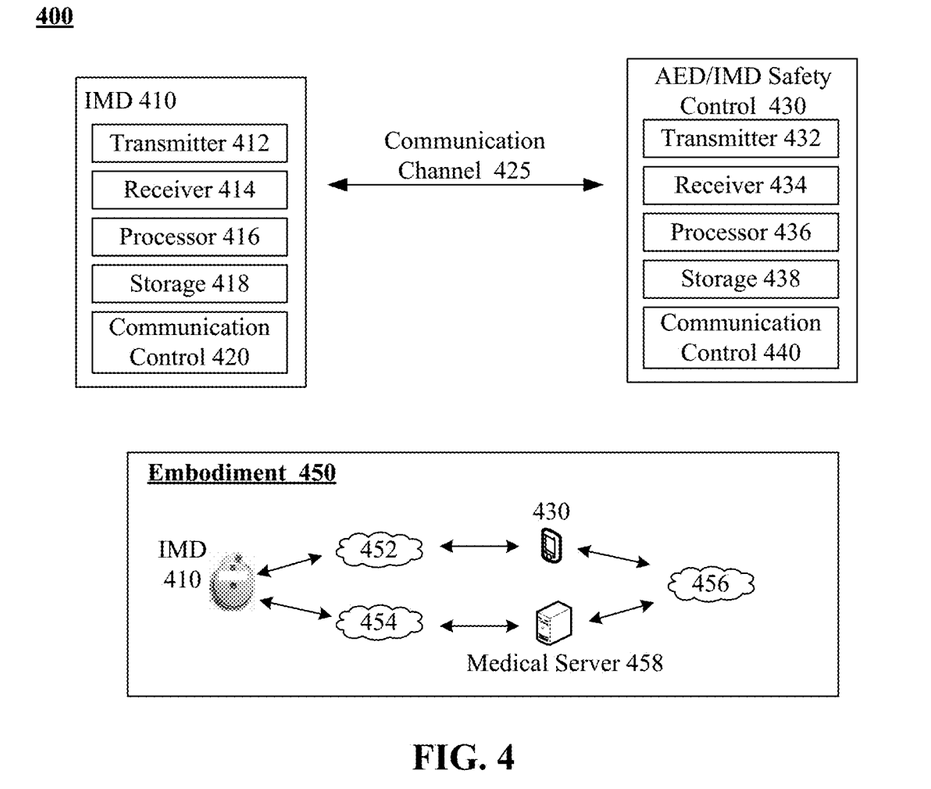
FIG. 4 is a diagram detailing communication capabilities between an exemplary implanted medical device and an automated external defibrillator having an IMD safety control in accordance with an embodiment of the disclosure.

FIG. 4 is a diagram 400 detailing communication capabilities between an exemplary implanted medical device 410 and an automated external defibrillator having an IMD safety control 430 in accordance with an embodiment of the disclosure. The concepts taught in the diagram 400 can be performed within the context of illustration 300 and/or utilizing steps described in methods 100, 200, 255, and/or 270.

The implanted medical device 410 can represent one specific embodiment of the implanted medical device 310 of illustration 300. Further, implanted medical device 410 can be an active implanted medical device having a transmitter 412, a receiver 414 (or both combined as a transceiver), one or more processors 416, storage 418, and communication control 420 circuits/program code, and the like. Similarly, the automated external defibrillator having the IMD safety control 430, can be configured to include a transmitter 432, receiver 434, processor 436, storage 438, communication control 440 circuits/program code, and the like.

The transmitters 412 and 432 and/or receivers 414 and 434 can provide for wireless communications. Communications to/from the implanted medical device 410 can occur over one or more communication channels 425. When multiple channels are used, different security measures and requirements can exist for these different communication channels 425. Further, different ones of these channels can be linked to different functions. That is, some protected functions may only be accessed over a specific channel, information of a particular type may be accessible over a different channel and not another, etc. Each of the different communication channels 425 can utilize secure transmission protocols to ensure data conveyed over each is protected during transmission. One or more encryption techniques can be used by one or more of the channels 425.

Any of a variety of cryptography techniques can be used to secure channels 425, such as use of hardware and/or software keys. Hardware based keys can be specifically useful, especially when the utilized keys for the channels 425 are never transported over a network, thus eliminating risks of interception of keys. A public key infrastructure (PKI) can be used to at least partially secure the channels 425 in one embodiment. The channels 425 can also utilize identity-based encryption (IBE), and PKI with an on-line trusted third party (TTP) based techniques.

In still another embodiment, biometric-based inputs and/or hardware keys unique to the automated external defibrillator having the IMD safety control 430, the implantee, and/or implanted medical device 410 can be utilized. For example, in one embodiment, a biometric input can be used to additionally secure one of the communication channels 425, which provides an additional level of assurance that the operator of the automated external defibrillator having the IMD safety control 430, through which sensitive personal and/or health data is provided, is an authorized information recipient.

Use of a short-range broadcast between the implanted medical device 410 and the automated external defibrillator having the IMD safety control 430 is another means of enhancing security when transmitting sensitive data from the implanted medical device 410. BLUETOOTH, WIRELESS USB, and other protocols (as well as derivatives thereof) exist that have a relatively short broadcasting range (under 10 meters, for example), which can be used for localized communications between implanted medical device 410 and the automated external defibrillator having the IMD safety control 430.

Similarly near field communications (NFC) can be used, which typically have a range of six inches or less to ensure that data is conveyed securely between the implanted medical device 410 and the automated external defibrillator having the IMD safety control 430. Use of a NFC can be especially useful in embodiments of the disclosure, as power required for data transmissions generally increases with distance and minimizing power of the implanted medical device 410 consumed for transmissions can be essential. When the automated external defibrillator having the IMD safety control 430 is able to communicate over a mobile telephony network, existing security protocols can be leveraged and enhanced (such as through a double-encryption scheme) to ensure channels 425 are secure.

Embodiment 450 is an example communication diagram illustrating network connectivity between an implanted medical device 410, a medical server 458, and the automated external defibrillator having the IMD safety control 430. A set of different networks 452, 454, 456 can interconnect these devices 410, 430, and 458. For example, network 452 can be a near field communication (NFC) or a personal area network. Network 454 can be a mobile telephony network, and network 456 can be an internet protocol (IP) network. In another embodiment, the illustrated networks 452, 454, 456 can be a common network.

Figure 4A:
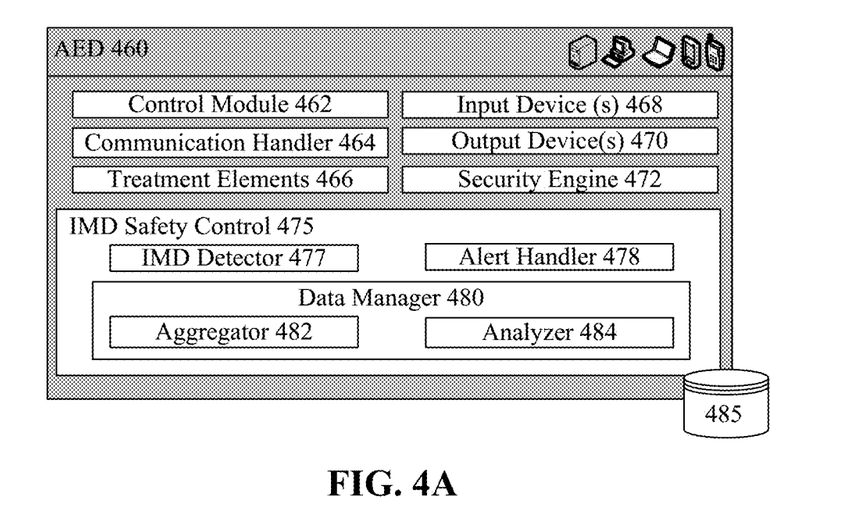
FIG. 4A is a block diagram of the automated external defibrillator having the IMD safety control in accordance with an embodiment of the disclosure.

As previously mentioned, the automated external defibrillator having the IMD safety control 430 can be a portable electronic device capable of administering defibrillation (e.g., a therapeutic electric shock). As shown in FIG. 4A, the automated external defibrillator 460, in general terms, can include components such as a control module 462, communication handler 464, treatment elements 466, input devices 468, output devices 470, security engine 472, the IMD safety control 475, and data store 485.

The control module 462 can represent the elements that control operation of the automated external defibrillator 460. To perform its functions, the control module 462 can include one or more processors, one or more nonvolatile memories, one or more volatile memories, digital signal processors, digital-to-analog converters, amplifiers, and other such components linked via a bus. Algorithms defining functions and analyses can be encoded in hardware, firmware, and/or software elements.

The communication handler 464 can include one or more receivers, transmitters, and/or transceivers. The communication handler 464 can enable wired and/or wireless communications of very short range (NFC range), short range (under 10 meters), medium range (WIFI range), and/or long range (cellular or mobile telephony).

The treatment components 466 can represent the elements required to provide an electric shock to the target person or implantee. Treatment components 466 can include, but are not limited to, a power source (e.g., battery), capacitors, charging circuits, shock delivery circuits, electrodes, an ECG circuit, an impedance circuit, a pacing circuit, and the like.

Many automated external defibrillators 460 currently available operate using a biphasic waveform like a biphasic truncated exponential (BTE) waveform; the concepts of this disclosure can also apply to those using a monophasic waveform. Because a biphasic waveforms defibrillate at lower energies, the treatment elements 466 required to generate the biphasic waveform can be smaller and less likely to cause injury due to over-defibrillation (i.e. damage to the heart muscle due to more electricity than necessary).

For example, the typical external defibrillator used in an emergency room drama that is charged to 360 Joules can be of the monophasic type, providing a high energy pulse that flows in one direction between the paddles or electrodes. The automated external defibrillator 460 available in many public places can administer an electric shock in the range of 50 Joules for children to 200 Joules for adults that flows in one direction between the electrodes for a predefined time period and then reverses flow for another time period.

Input devices 468 can include buttons, dials, a touch pad, a touch screen, a keyboard, a microphone for speech input, a biometric sensor, a camera, an accelerometer, and the like. Output devices 470 can include a display, a speaker, a voice synthesizer, a vibration generator, and the like. The security engine 472 can encrypt/decrypt data, which includes data sent from the implanted medical device 410.

The IMD safety control 475 can include components such as an IMD detector 477, alert handler 478, and data manager 480. The IMD detector 477 can be the components utilized in detecting the presence of implanted medical device 410 within the target person. The IMD detector 477 can follow predefined standards in the art for identifying the presence of an implanted medical device 410 like those described in methods 255 and 270.

The data manager 480 can utilize an aggregator 482 and analyzer 484 to determine if the shock function has the potential to harm the implantee or implanted medical device 410. The aggregator 482 can be configured to collect pertinent data from trusted data sources, like medical server 458 and data store 485. The analyzer 484 can determine if the operation of the implanted medical device 410 or the health of the implantee could be adversely affected by the shock function using the current configuration (i.e., pad placement, parameters).

The data manager 480 can invoke the alert handler 478 when potentially adverse conditions are identified. The alert handler 478 can utilize the output devices 470 to display a message to the operator as well as trigger an audible and/or visual alarm of the automated external defibrillator 460, when available. Depending upon the specific configuration and capabilities of the automated external defibrillator 460, the alert handler 478 can also convey a message over one or more networks 452-456 to another electronic device like a page or text message to a doctor or nurse or a phone call to an emergency number (911).

The alert handler 478 can also be responsible for interacting with the control module 462 to disable or lock-out one or more treatment elements 466, as well as releasing the treatment elements 466 once resolution of the identified problem has been entered by the operator and/or once interference with the implanted medical device 410 is minimized.

In the embodiment of the IMD safety control 475 shown in FIG. 4A, the IMD safety control 475 can utilize components of the automated external defibrillator 460 like the communication handler 464, input devices 468, output devices 470, and elements of the control module 462.

In another contemplated embodiment, the IMD safety control 475 can be an independent device that is coupled with or connected to the automated external defibrillator 460. In such an embodiment, the IMD safety control 475 can have a separate control module 462 and communication handler 464, interfacing with the automated external defibrillator 460 to perform input/output and control functionalities.

In yet another contemplated embodiment, the IMD safety control 475 can utilize the automated external defibrillator 460 and its treatment elements 466 to replace the functionality of a cardiac-related implanted medical device 410, such as a pacemaker or ICD. In such an embodiment, the IMD safety control 475 can instruct the implanted medical device 410 to place itself in a "safe" mode (i.e., not actively providing treatment) and instruct the automated external defibrillator 460 to provide related monitoring and treatment. This embodiment can be particularly beneficial and easy to implement since many automated external defibrillators 460 already include the ability to perform transcutaneous cardiac pacing.

As used herein, presented storages 418 and 438 and data store 485 can be a physical or virtual storage space configured to store digital information. Storages 418 and 438 and data store 485 can be physically implemented within any type of hardware including, but not limited to, a magnetic disk, an optical disk, a semiconductor memory, a digitally encoded plastic memory, a holographic memory, or any other recording medium. Storages 418 and 438 and/or data store 485 can be formed from a plurality of physical devices. Additionally, information can be stored within storages 418 and 438 and data store 485 in a variety of manners. For example, information can be stored within a database structure or can be stored within one or more files of a file storage system, where each file may or may not be indexed for information searching purposes. Further, storages 418 and 438 and/or data store 485 can utilize one or more encryption mechanisms to protect stored information from unauthorized access.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for mitigating interference of an automated external defibrillator with operation of an implanted medical device (IMD) comprising:

in response to an attachment of an automated external defibrillator to a living body having an implanted medical device embedded therein, herein referred to as an implantee, detecting of said implanted medical device (IMD) of the implantee by an IMD safety control module coupled with the automated external defibrillator, wherein performance of a shock function by the automated external defibrillator is known to have a potential to cause at least one adverse effect to at least one of a treatment provided by the implanted medical device and operation of the implanted medical device, wherein the implanted medical device is an active implanted medical device having wireless communication capabilities;

establishing a communication pathway with the detected implanted medical device, wherein the communication pathway for wireless communication refers to any communication medium not requiring a dedicated physical wire between communication endpoints over which an information bearing signal is conveyed;

disabling performance of the shock function of the automated external defibrillator, wherein the disabling automatically occurs by default responsive to a wireless communication between the automated external defibrillator and the implanted medical device via the established communication pathway and does not require visual inspection of the implantee by an operator of the automated external defibrillator for at least one of post-operation indicators for the implanted medical device and an indicia for the implanted medical device worn by the implantee;

requesting resolution from the operator of the automated external defibrillator to accommodate the implanted medical device detected within the implantee; and upon receipt of said resolution, enabling performance of the shock function by the automated external defibrillator.

2. The method of claim 1, wherein detecting the implanted medical device further comprises:

broadcasting a request for identification from implanted medical devices within the implantee upon communication channels known to be utilized by implanted medical devices; and receiving an identification response from at least one implanted medical device, wherein receipt of the identification response is considered as the detection of the implanted medical device.

3. The method of claim 1, wherein disabling the performance of the shock function further comprises:

requesting at least one of patient data and operational data from the implanted medical device;

upon receipt of the requested data, determining a likelihood that the performance of the shock function by the automated external defibrillator to have an adverse effect upon at least one of operation of the detected implanted medical device and the implantee;

when the determined likelihood meets or exceeds a predefined threshold, proceeding with the disablement of the performance of the shock function of the automated external defibrillator; and when the determined likelihood is less than the predefined threshold, cancelling the disabling of the performance of the shock function, requesting of resolution from the operator, and enabling of the performance of the shock function, wherein operation of the automated external defibrillator is uninterrupted.

4. The method of claim 3, wherein determining the likelihood of the adverse effect further comprises:

aggregating data for at least one of the implantee's health, the shock function of the automated external defibrillator, and a parameter of a current configuration of the automated external defibrillator from at least one external data source; and calculating the likelihood of the adverse effect using the aggregated data and a predefined formula.

5. The method of claim 4, further comprising:

analyzing the aggregated data;

based upon said analysis of the aggregated data, determining that the automated external defibrillator is capable of performing a function substantially similar to that of the implanted medical device;

conveying a command to the implanted medical device via the established communication pathway to pause operation of the implanted medical device; and providing the substantially similar function to the implantee, when necessary, wherein the automated external defibrillator coordinates provision of the shock function and the substantially similar function to avoid interference of both functions.

6. The method of claim 1, wherein disabling performance of the shock function further comprises:

conveying of a command by the IMD safety control to a control module of the automated external defibrillator, wherein execution of the conveyed command by the control module results in a suspension of the shock function currently being performed.

7. The method of claim 1, wherein requesting resolution from the operator further comprises:

presenting a message within a display area of the automated external defibrillator, wherein the message indicates an existence of the implanted medical device within the implantee and at least one means to mitigate causing the at least one adverse effect; and emitting an audible sound alert.

8. The method of claim 1, wherein the resolution comprises modifying at least one parameter of the shock function.

9. The method of claim 1, wherein detection of the implanted medical device utilizes a near field communication (NFC) transmission.

10. The method of claim 1, wherein the implanted medical device is one of a neurostimulator, a cardioverter-defibrillator, a cardiac resynchronization device, a pacemaker, and a medical pump.

11. A computer program product comprising a computer readable storage medium having computer usable program code embodied therewith, the computer usable program code comprising:

computer usable program code configured to, in response to an attachment of an automated external defibrillator to a living body having an implanted medical device embedded therein, herein referred to as an implantee, detect said implanted medical device (IMD) of the implantee, wherein performance of a shock function of the automated external defibrillator is known to have a potential to cause at least one adverse effect to at least one of a treatment provided by the implanted medical device and operation of the implanted medical device, wherein the implanted medical device is an active implanted medical device having wireless communication capabilities;

computer usable program code configured to establish a communication pathway with the detected implanted medical device, wherein the communication pathway for wireless communication refers to any communication medium not requiring a dedicated physical wire between communication endpoints over which an information bearing signal is conveyed;

computer usable program code configured to disable performance of the shock function of the automated external defibrillator, wherein the disabling automatically occurs by default responsive to a wireless communication between the automated external defibrillator and the implanted medical device via the established communication pathway;

computer usable program code configured to request resolution from the operator of the automated external defibrillator to accommodate the implanted medical device detected within the implantee; and computer usable program code configured to, upon receipt of said resolution, enable performance of the shock function by the automated external defibrillator.

12. The computer program product of claim 11, wherein disabling the performance of the function by the electronic device further comprises:

computer usable program code configured to convey a command to a control module of the automated external defibrillator, wherein execution of the conveyed command by the control module results in disabling performance of the shock function.

13. An article of manufacture comprising:

special purpose hardware; and a storage medium storing instructions, which when executed by the special purpose hardware result in the special purpose hardware performing specialized functions comprising:

in response to an attachment of an automated external defibrillator to a living body having an implanted medical device embedded therein, herein referred to as an implantee, detecting of said implanted medical device (IMD) of the implantee by an IMD safety control module coupled with the automated external defibrillator, wherein performance of a shock function by the automated external defibrillator is known to have a potential to cause at least one adverse effect to at least one of a treatment provided by the implanted medical device and operation of the implanted medical device, wherein the implanted medical device is an active implanted medical device having wireless communication capabilities;

establishing a communication pathway with the detected implanted medical device, wherein the communication pathway for wireless communication refers to any communication medium not requiring a dedicated physical wire between communication endpoints over which an information bearing signal is conveyed;

disabling performance of the shock function of the automated external defibrillator, wherein the disabling automatically occurs by default responsive to a wireless communication between the automated external defibrillator and the implanted medical device via the established communication pathway and does not require visual inspection of the implantee by an operator of the automated external defibrillator for at least one of post-operation indicators for the implanted medical device and an indicia for the implanted medical device worn by the implantee;

requesting resolution from the operator of the automated external defibrillator to accommodate the implanted medical device detected within the implantee; and upon receipt of said resolution, enabling performance of the shock function by the automated external defibrillator.

14. The article of manufacture of claim 13, wherein the special purpose hardware is hardware of the automated external defibrillator.

15. The article of manufacture of claim 13, wherein the specialized hardware comprises leads that attach to the implantee, wherein the shock function for defibrillation is delivered through the leads by the specialized hardware.

16. The article of manufacture of claim 13, wherein the specialized hardware comprises hardware components that generate and deliver electricity for the shock function.

17. The article of manufacture of claim 13, wherein the instructions are embedded within firmware, wherein the storage medium is a read only memory.

* * * * *